March 5, 1940. L. M. RECTOR Plant Pat. 365
PAPAVER OR POPPY
Filed July 14, 1939
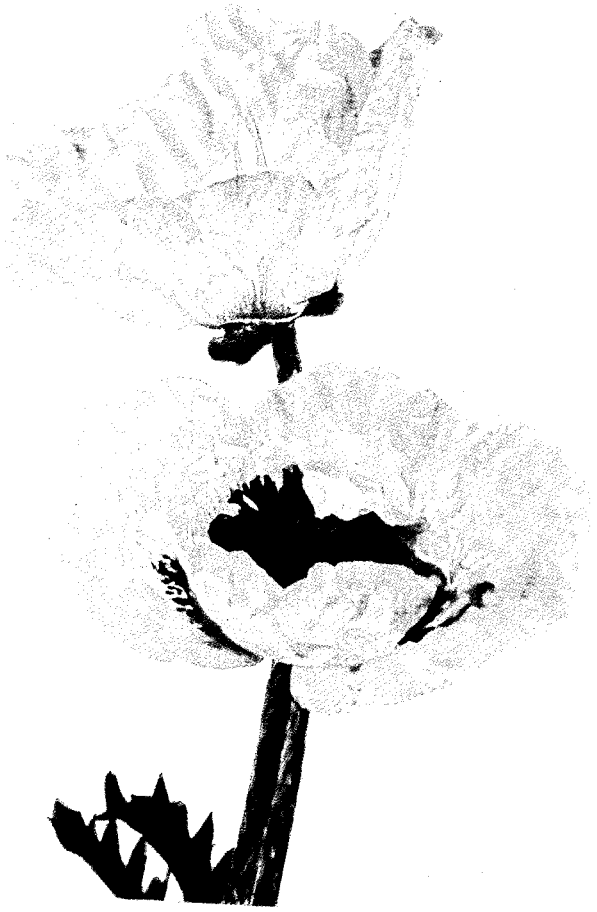
INVENTOR
LULU M. RECTOR
BY John A. Leonard
HER ATTORNEY Patented Mar. 5, 1940

Plant Pat. 365

UNITED STATES PATENT OFFICE

365

PAPAVER OR POPPY

Lulu M. Rector, Clarksburg, W. Va., assignor to Wayside Gardens Company, Mentor, Ohio, a corporation of Ohio Application July 14, 1939, Serial No. 284,528

1 Claim. (Cl. 47—60)

This invention relates to a new and distinct variety of poppy of the "Papaver" genus and of the *"orientale"* species, and has as its principal object the origination of an *"orientale"* poppy that bears flowers having petals, each of which are of a two-color combination, or of a so-called two-tone color, and the color combination is of colors which are contrasting, attractive and appropriate for garden decorative purposes.

In producing this variety, I chose, as the pollen parent, the more or less delicate variety "Perry's White" which is characterized by its fine satiny white flowers, and as the seed parent, the variety "Mrs. Perry" which, as one of the pink poppies, is characterized for its robust nature. Since the original production of the new variety, many plants have been asexually reproduced from the original plant, and each of them has borne flowers true to the description hereinafter made.

The distinctiveness of the variety resides in the color of the flowers appearing on the plant in that each flower is of a two-color combination, or as ordinarily termed, a two-tone color. The upper part of the petals is of a more or less flame orange, comparable to Maerz & Paul Plate No. 3–K–12, and the lower or base part is a white, comparable to Maerz & Paul Plate No. 1–A–1, which, in some instances, has a somewhat faint vein-like orange coloring appearing therein, but which is not so intense as to affect the distinct orange and white two-tone color if the flower is viewed from a distance.

The plant, being of the *orientale* species, possesses its distinctive characteristics, such as the relatively large blooms which, in this instance, are 3'' to 4'' in diameter and 2½'' to 3½'' deep, and the rather sturdy stems 24 to 30'' high bearing the blooms and supporting them in a substantially upright position. Additionally, the plant, of a compact nature, is a dwarf growth producing at one time as many as ten to fifteen stems bearing flowers. The foliage, of relatively short leaves, has pubescent surfaces and is of a dark Taxus-Green color comparable to Maerz & Paul Plate No. 24–L–12. The stems are of a similar color. The flowering period takes place in early June and the flowers produced have, on the plant, a lasting quality better than most varieties. Generally speaking, the growing characteristics of the plant and the distinctiveness and vivid coloring of the blooms make the variety useful for garden decorative purposes.

Having now fully shown and described my new variety of Oriental poppy, and its manner of production and the distinctiveness of coloring, in addition to the description heretofore given, being illustrated by the drawing as true as can be by water color reproduction, what I claim and desire to secure by Letters Patent of the United States is:

An Oriental poppy substantially as herein shown and described and characterized by the two-color combination of flower comprising an upper part of a flame orange color and a lower part of white.

LULU M. RECTOR.